US00PP28359P3

(12) United States Plant Patent
Salvi

(10) Patent No.: US PP28,359 P3
(45) Date of Patent: Sep. 5, 2017

(54) APPLE TREE NAMED 'MILLY'

(50) Latin Name: ***Malus domestica* Borkh**
Varietal Denomination: MILLY

(71) Applicant: Luigi Salvi, Ferrara (IT)

(72) Inventor: Luigi Salvi, Ferrara (IT)

( * ) Notice: Subject to any disclaimer, the term of this patent is extended or adjusted under 35 U.S.C. 154(b) by 78 days.

(21) Appl. No.: 14/545,196

(22) Filed: Apr. 7, 2015

(65) Prior Publication Data

US 2015/0289428 P1 Oct. 8, 2015

(30) Foreign Application Priority Data

Apr. 8, 2014 (QZ) ..... PRB 2014/0964

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Keith Robinson
(74) *Attorney, Agent, or Firm* — Foley & Lardner LLP

(57) ABSTRACT

A new and distinct *Malus domestica* Borkh apple tree variety named 'MILLY', particularly characterized by its medium-strong vigor and early and constant production. Fructification is precocious, and the productivity is high. The fruits have medium to big size, are slightly asymmetric, with an attractive red-purple color on 50-60% of the surface. The flesh is crispy, juicy and firm and has a mild flavor. The taste is very good and the aroma is mild, slightly acid to sweet, with a good sugar content with balanced acidity level. Good tendency to long term storage.

5 Drawing Sheets

Latin name of the genus and species of the plant claimed: *Malus domestica* Borkh.
Variety denomination: 'MILLY'.

PRIORITY CLAIM

This application claims priority to European Community Plant Variety Office Application No. 2014/0964 filed Apr. 8, 2014, the entire contents of which are incorporated by reference herein in their entirety.

BACKGROUND OF THE INVENTION

This invention relates to a new and distinct variety of apple tree, botanically known as *Malus domestica* Borkh of the Rosaceae family, and hereinafter referred to by the variety denomination 'MILLY'.

The new *Malus* variety was discovered and selected by the inventor, Luigi Salvi, as a mutation of 'CRIPPS PINK' (Patented, U.S. Plant Pat. No. 7,880), growing in a cultivated area in Ferrara, Italy. The new *Malus* variety was selected by the inventor based on constant and early production, 3 to 4 weeks before 'CRIPPS PINK'.

Asexual reproduction of the new *Malus* variety by budding and grafting was first performed in August 2012 in Consandolo, Ferrara, Italy, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'MILLY' which in combination distinguish this Apple tree as a new and distinct variety:

1. Red-purple color;
2. Big size, solid flush with weakly defined stripes;
3. Weak vigor, open habit with short branches, easy to manage;
4. High sugar content; and
5. Long storage ability.

In comparison to the parental and commercial varieties known to the present inventor, the most similar is the parent variety 'CRIPPS PINK'. When the claimed variety 'MILLY' and the parent variety are compared, they differ primarily in the traits listed in Table 1.

TABLE 1

Comparison with parent and similar variety

| Trait | New Variety 'MILLY' | Parent Variety 'CRIPPS PINK' |
|---|---|---|
| Time of eating maturity | Late (2-10 October in Ferrara, Italy) | Very late—3-4weeks after Milly in Ferrara, Italy |
| flowering | Very high flowering | Good flowering |
| Fruit Production | Constant production | Some biennial bearing |
| Fruits size | Medium-big size | Medium size |
| Branch Angle | 50-55° at the inside measurement | Slightly less open than 'MILLY' |

BRIEF DESCRIPTION OF THE PHOTOGRAPHS

The accompanying photographs illustrate the overall appearance of the new *Malus* variety 'MILLY' showing the colors as true as is reasonably possible with colored reproductions of this type. Colors in the photographs may differ slightly from the color values cited in the detailed botanical description, which accurately describe the color of 'MILLY'. The age of the trees shown in the photographs is approximately 3 years.

Figure 1:
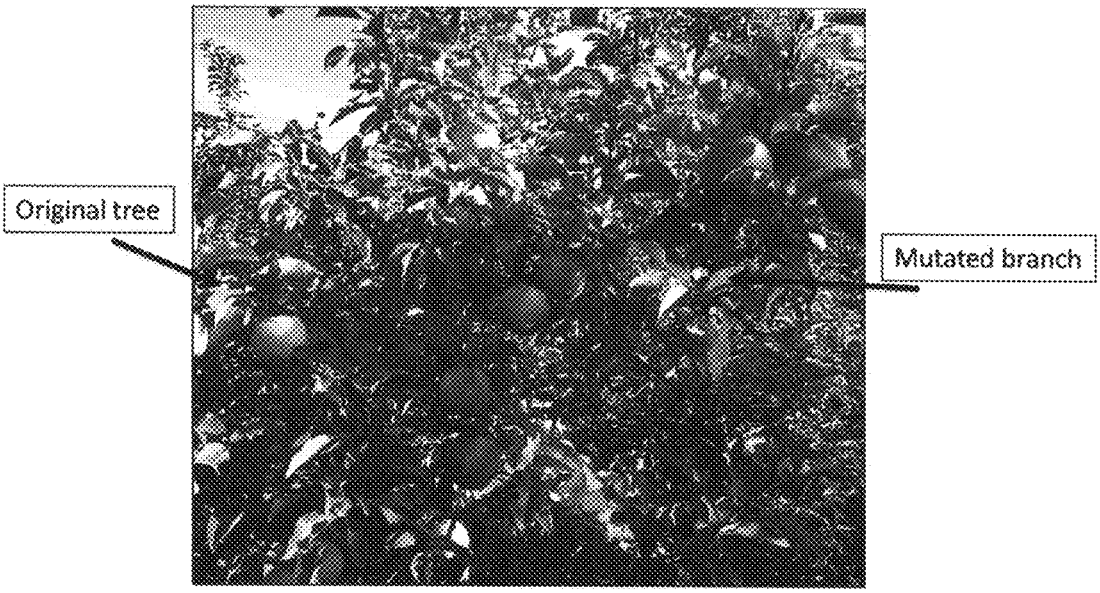

FIG. 1—Shows a mutated branch, right, and the original tree, left.

Figure 2:
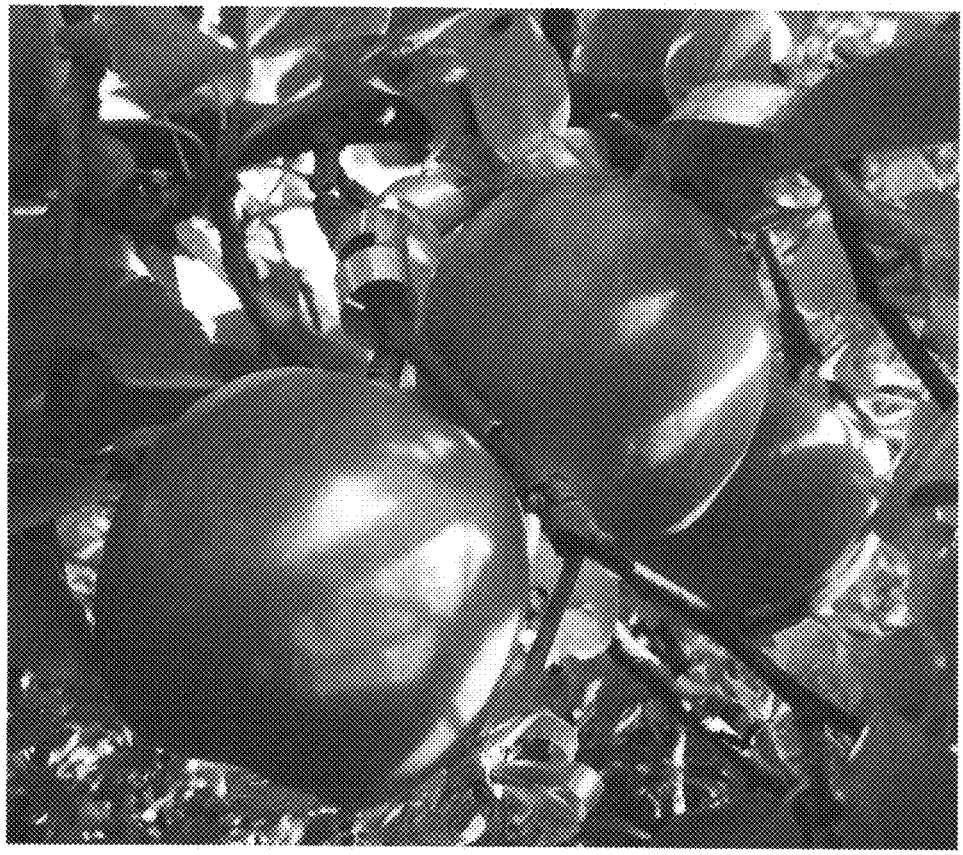

FIG. 2—Shows typical fruit of 'MILLY'.

Figure 3:
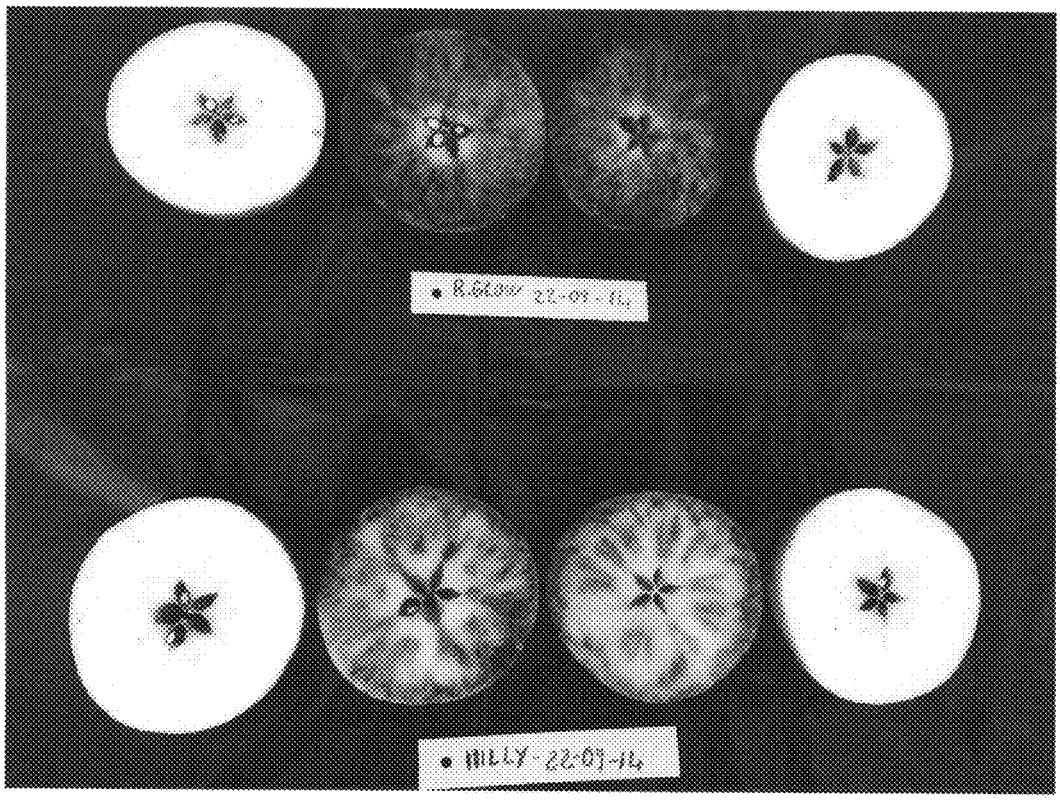

FIG. 3—Shows the fruit of 'MILLY' at different stages of maturity.

Figure 4:
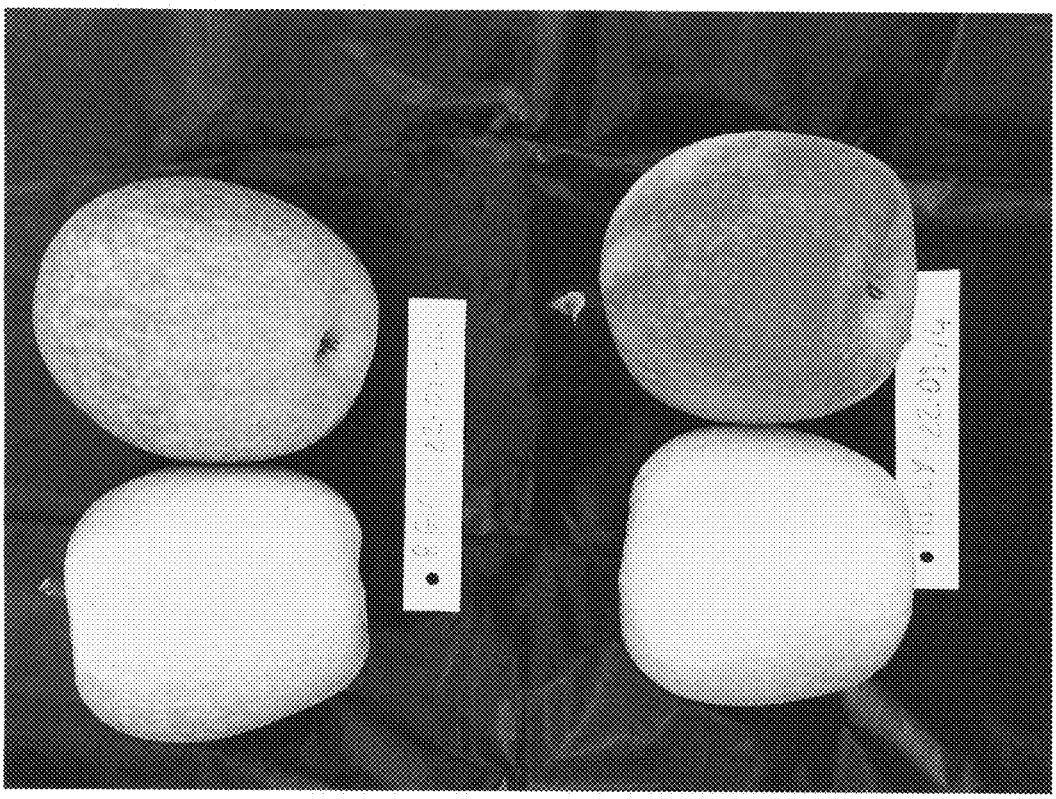

FIG. 4—Shows the fruit colors of 'MILLY'.

Figure 5:
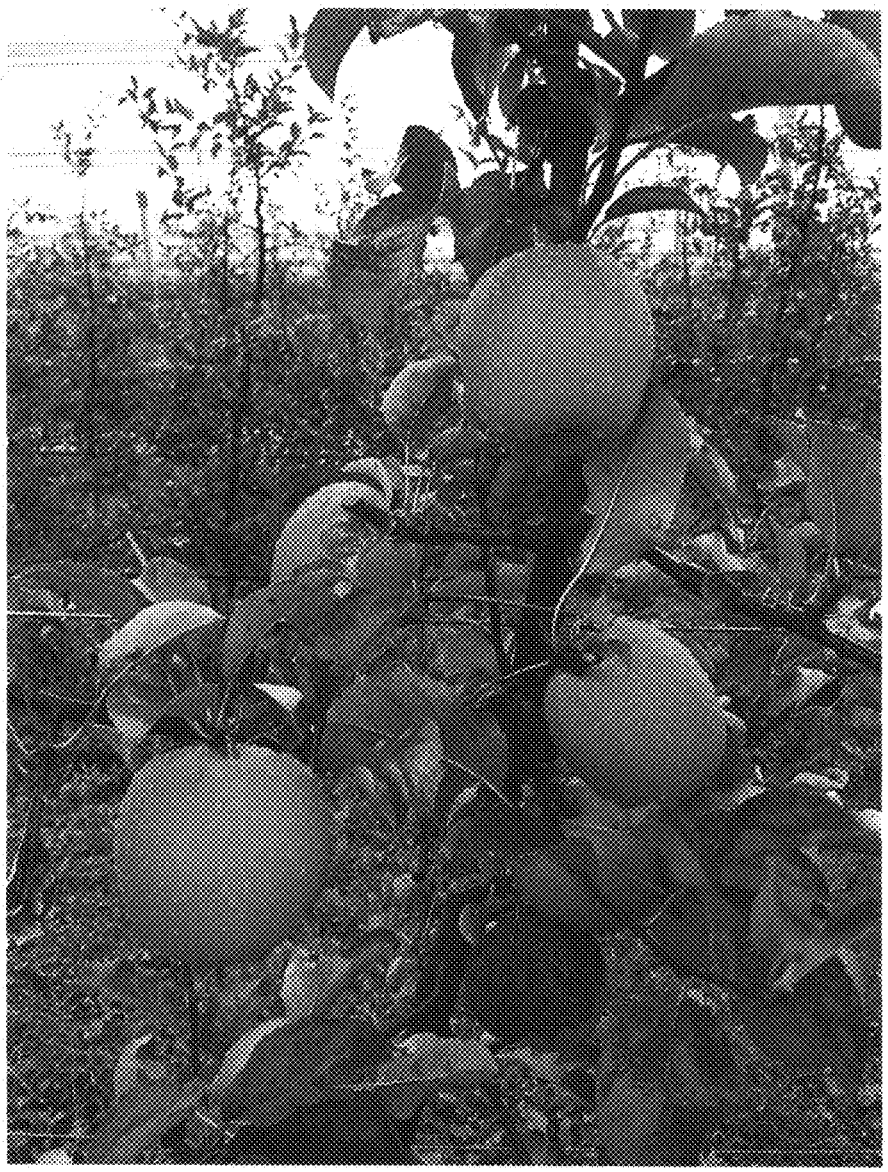

FIG. 5—Shows the fruit of 'MILLY' on the plant.

DETAILED BOTANICAL DESCRIPTION

The new *Malus* variety 'MILLY' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'MILLY' as grown in the apple farm in Consandolo, Ferrara, Italy, under conditions which closely approximate those generally used in commercial practice. The Apple farm where 'MILLY' is grown is situated 30 km from the Adriatic sea (44° 65' North, 11° 76' East) and is 4 meters above sea level. The soil of apple farm where 'MILLY' is grown is middle clay, the soil is treated with manure and irrigated with drip irrigation systems. The climate is temperate continental with high summer temperatures and low winter temperatures.

Unless otherwise stated, the detailed botanical description includes observations, measurements and values based on 3 year old 'MILLY' trees that were grown in the Apple farm from Consandolo, Ferrara, Italy from 2012 to 2014. Quantified measurements are expressed as an average of measurements taken from a number of trees of 'MILLY'. The measurements of any individual tree, or any group of trees, of the new variety may vary from the stated average.

Color references are made to The Royal Horticultural Society Colour Chart (R.H.S.) 2001 edition, except where general colors of ordinary significance are used. Color values were taken under daylight conditions at approximately at 10:00 a.m. in Consandolo—Ferrara—Italy.

All of the trees of 'MILLY', insofar as they have been observed, have been identical in all the characteristics described below.

Classification:

*Botanical.*—*Malus domestica* Borkh.

Parentage: Limb sport mutation of *Malus domestica* variety designated 'CRIPPS PINK'.

Propagation: Budding and grafting on M9 T337 rootstock.

Growing conditions:

*Light intensities.*—Full sunlight.

*Temperature.*—During day, grown in range of 15° C. to 25-35° C. (maximum in summer), and during evening, grow in range of −5° C. to 15° C. (autumn/winter period).

*Fertilization.*—A balanced fertilizer with level of N=25 KG/HA. P=10 KG/HA. K=30 KG/HA.

*Growth regulators.*—None.

*Pruning or trimming requirements.*—Standard pruning and growing conditions.

Tree:

*Age.*—Observed trees were 3 years old.

*Vigor.*—Medium-strong vigor; abundant flowering; early beginning production; good production.

*Form.*—Upright spreading and conical.

*Habit.*—A average size tree with one medium stocky trunk and smooth; main branches spreading.

*Branching habit.*—Main branches angle is 55° to 85° with respect to trunk if allowed to grow naturally.

*Density.*—Medium density; about 3000 trees per hectare.

*Cropping behavior.*—Precocious fruit bearing with high productivity.

*Type of bearing.*—Early beginning of production; no biennial bearing. Production of 3 years old plants: about 10-11 kg.

*Size at maturity.*—Height: (on 3 years old tree) About 2.4 m. Spread: About 1 m.

*Trunk.*—Height (up to leaders): About 2.4 m. Diameter: About 40 mm as measured 20 cm above point of grafting. Texture: At first, smooth with numerous lenticels, then shallow furrows and scaly ridges. Bark color: Primarily grey-brown with RHS 199 C, underbark. Trunk Lenticels: Length: 2.5 mm. Width: 1.8 mm. Color: greyed-brown RHS 199B. Density: about 3 per $cm^2$.

*Branches.*—Number per tree: About 15 at 3 years. Length: Varies due to pyramidal shape of tree; maximum of 80 cm to 100 cm; minimum of 40 cm to 50 cm. Diameter (at 3 years): About 10 mm to 12 mm. Surface texture: smooth. Pubescence: moderate pubescence on new wood. Color: Mature (after about 3 year old): grey-brown RHS 199 C. New Growth: RHS 183 A. Internode length: About 20 cm to 32 cm. Internode diameter: About 8 mm to 12 mm. Branch lenticels: Length: About 1.0 mm. Width: About 0.5 mm. Color: RHS 155 C. Density: About 7-8 per $cm^2$.

*Spur.*—Present: Yes. Distance between each spur: On the 3 year old branches, the distance is about 39 mm to 40 mm. Diameter of each spur: About 4 mm. Number of fruit per spur: About 2 to 4.

Foliage:

*Arrangement.*—Alternate, simple, petiolated.

*Lamina.*—Size: from the observation of 10 fully expanded leaves in September 2014 in Consandolo, Ferrara, Italy. Length: About 102 mm (from 4th to 6th fully expanded leaf). Width: About 59 mm (from 4th to 6th fully expanded leaf). Length/width ratio: 1.72. Overall Shape: large — elliptical, wide, oval, convex, pointed, medium thick, smooth. Base shape: broad. Apex shape: accuminate. Margin: finely serrate, crenate. Texture: Upper surface: smooth. Under surface: matte and pubescent. Attitude in relation to shoot: outwards. Color (mature leaves): Upper surface: RHS 139 A — green. Under surface: RHS 148 B. Color (immature leaves): Upper surface: RHS 141 A — green. Under surface: RHS 138 A.

*Venation.*—Type: light green venation from central vein to the leaf edge. Color: RHS 195 A — greyed-green.

*Petiole.*—Length: average 33 mm. Diameter: average 1.9 mm. Texture: slightly pubescent. Color: RHS 184B.

*Stipule.*—Arrangement: adnate, grown together; medium size. Length (distance of stipules from basal attachment of petiole): About 5 mm to 10 mm. Width: About 0.9 mm to 1.4 mm.

Inflorescence:

*Blooming time.*—Full bloom on about March 28th to 13th April.

*Blooming period*.—About 12 to 15 days.
*Fragrance*.—Slight.
*Type*.—Corymbe.
*Number of flowers per inflorescence*.—About 5 to 6.
*Inflorescence size*.—Diameter: About 45 mm.
*Buds*.—Terminal Buds: Number per spur: one per spur. Shape: ellipsoid. Length: About 9 mm. Width: About 4 mm. Texture: slightly pubescent. Color: Apex, greyed-purple RHS 187 B, and base, RHS 197 B.
*Petals*.—Arrangement: touching to overlapping. Size: Length: About 25 mm. Width: About 16 mm. Length/width ratio: 1.56. Overall shape: ovate. Apex shape: rounded. Base shape: rounded. Texture (upper surface): smooth. Texture (lower surface): smooth. Margin: ruffled. Color (at balloon stage): red, RHS 58C. Color (upper surface): white Apex RHS 155C, and traces of red-purple RHS 65 C. Color (lower surface): white Apex, RHS 155C, and traces of red-purple RHS 68 C.
*Sepals*.—Number per flower: Five. Size: Length: About 8 mm. Width: About 3.6 mm. Length/width ratio: 2.2. Overall shape: pointed, acuminate, recurved downward. Apex shape: acuminated. Base shape: slightly flattened. Texture (upper surface): pubescent. Texture (lower surface): pubescent. Margin: smooth. Color (upper surface): green RHS 135C. Color (lower surface): green RHS 135C.
*Pedicel*.—Length: 25 to 29 mm. Diameter: about 2 mm. Texture: hairy. Color: grey-green RHS 138C.

Fruit:
*Keeping quality*.—The fruit keeps very well on the tree. It can be stored in cold temperature conditions for up to 6 months without losing firmness and juiciness. It has a shelf life up to 2 weeks without losing firmness and juiciness.
*Maturity when described*.—Ripe for eating by early October up to time of harvest.
*Maturity period after full bloom*.—About 180-195 days after full bloom on April 4th.
*Date of first and last picking* (*harvest*).—About 2nd October to 10th October in Consandolo, Ferrara, Italy.
*Type*.—Pome.
*General shape*.—Round, oblong, usually asymmetric, with non-prominent lobes at calyx ends.
*Average weight*.—About 185 to 200 g.
*Fruit size*.—Average height: About 78.5 mm. Average diameter (at widest point): About 82 mm. Position of maximum diameter: at about ½ of height near stem end. Height/thickness ratio: 0.95.
*Stem*.—Length: About 20-25 mm. Diameter: About 2.6 mm. Color: yellow-green RHS 145 C.
*Stalk*.—Length: 19-24 mm. Thickness: 3-4 mm.
*Stalk cavity*.—Depth: About 18 mm. Width: About 19 mm.
*Eye basin*.—Depth: About 12 mm. Width: About 28 mm. Crowning at calyx end: medium. Position of sepals: Half-closed. Calyx tube: funnel form.
*Eye*.—Depth: 1.6 cm. Width: 2.4 cm.
*Russet area*.—Absent.
*Skin*.—Thickness: medium. Texture: smooth or slightly rough. Bloom: absent. Greasiness: absent or very weak. Firmness (at picking time): 8 to 9 kg/cm2. Overcolor Color: RHS N57C red purple. Percentage of skin surface with overcolor color: medium large 50% to 60%. Pattern of overcolor: blushed and lightly striped; stripe thickness about 1 mm. Intensity of overcolor: medium. Ground color: RHS 145C. Skin Lenticels: Length: About 0.7 mm. Width: About 0.6 mm. Color: RHS green-white 157 D. Density: About 1.8 per $cm^2$.
*Flesh*.—Color: yellow-white RHS 11 D. Texture: crisp and juicy — firm. Aroma: mild aroma. Eating quality: slightly acidic to sweet, suave and fragrant. Sugar content (at picking time): 13 to 16 Brix. Acidity/Starch (at picking time) 4.6 to 5.7 g/lt Malic acid/starch: 3 (Lainburg scale). Core: Symmetry of core: slightly asymmetric. Distinctness of core lines: meeting, heart-shaped. Locules: Number (per fruit): 5 (five). Length: About 9-10 mm. Width: About 4-5 mm. Form: moderately open.

Seeds:
*Number per fruit*.—About 7 to 9.
*Number per locule*.—About 1 - 2.
*Shape*.—Elliptic, acute at point.
*Length*.—About 8-8.5 mm.
*Width*.—About 5 mm.
*Color*.—RHS 165A.

Reproductive organs:
*Androecium*.—Stamen: Number per flower: about 17-20. Length: About 12 mm.
*Anther*.—Number: about 15 per flower. Shape: ovoid. Length: About 2 mm. Color: yellow RHS 10 B. Filaments: Length: About 10 mm. Pollen: Amount: abundant. Color: RHS 1C. Pollination Requirements: the *Malus domestica* variety 'Granny Smith' is good pollinator.
*Gynoecium*.—Stigmas: Shape: funnel shape with receptive surface on top. Length: About 1 mm. Width: About 0.6 mm. Color: yellow, RHS 1C. Ovary: Length: About 3.5 to 4 mm. Width: About 2.5 mm. Color: yellow-green, RHS 144 A.

Use: Fresh market.
Disease/pest resistance: None noted.
Disease/pest susceptibility: No particular sensibilities detected.
Winter hardiness: Tolerant to temperatures down to −15° C. without observed damage to wood and buds of dormant Apple trees; but open flowers and young fruitlets are damaged by exposure to −3° C. to −5° C., depending on the length of exposure.
Drought/heat tolerance: Tolerant to temperatures up to 40° C., growth is limited by drought periods without irrigation.
Shipping/storage characteristics: Very good storability under ULO-conditions (1° C., 2% O2 , 2% CO2) for up to seven (7) /months.

I claim:
1. A new and distinct variety of *Malus domestica* Borkh apple tree named 'MILLY', as illustrated and described herein.

* * * * *